(12) United States Patent  (10) Patent No.: US 8,487,776 B2
Livchak et al.  (45) Date of Patent: Jul. 16, 2013

(54) DUCT GREASE DEPOSIT DETECTION DEVICES, SYSTEMS, AND METHODS

(75) Inventors: Andrey V. Livchak, Bowling Green, KY (US); Derek W. Schrock, Bowling Green, KY (US)

(73) Assignee: Oy Halton Group Ltd., Vantaa (FI)

( * ) Notice: Subject to any disclaimer, the term of this patent is extended or adjusted under 35 U.S.C. 154(b) by 452 days.

(21) Appl. No.: 12/664,369

(22) PCT Filed: Jun. 13, 2008

(86) PCT No.: PCT/US2008/067000
§ 371 (c)(1), (2), (4) Date: May 5, 2010

(87) PCT Pub. No.: WO2008/157418
PCT Pub. Date: Dec. 24, 2008

(65) Prior Publication Data
US 2010/0225477 A1  Sep. 9, 2010

Related U.S. Application Data

(60) Provisional application No. 60/943,626, filed on Jun. 13, 2007.

(51) Int. Cl.
*G08B 21/00* (2006.01)
(52) U.S. Cl.
USPC ............ 340/607; 340/540; 340/608; 340/619
(58) Field of Classification Search
USPC ................ 340/540, 603, 606, 607, 608, 612, 340/619
See application file for complete search history.

(56) References Cited

U.S. PATENT DOCUMENTS 3,023,312 A 2/1962 Wood
3,810,009 A * 5/1974 Hausler et al. ................... 374/7

(Continued)

FOREIGN PATENT DOCUMENTS

DE 195 10 304 C1 2/1996
EP 0 706 045 B1 1/2002

(Continued)

OTHER PUBLICATIONS

Supplementary European Search Report dated Jun. 2, 2010 for Application No. EP 08771092.

(Continued)

*Primary Examiner* — George Bugg
*Assistant Examiner* — Naomi Small
(74) *Attorney, Agent, or Firm* — Miles & Stockbridge, P.C.; Mark A. Catan

(57) ABSTRACT

Automatic devices that determine when pollutant deposits have accumulated in ductwork may be employed to notify maintenance personnel or automated cleaning equipment of the need for ducts to cleaned or replaced. Various detection devices may be employed to detect a property of accumulated grease and generate an indication of an accumulation. The detection device may present a surface to the fume stream inside a duct. The surface may be cooled to a temperature that represents a worst case temperature so that the accumulation due to condensation on the detector surface is at least as high as the coolest surface in the ductwork which is being monitored. Alternatively, the detection device may be located external to the duct. The detection device may interrogate the surface of the duct through contact or noncontact measurements to determine the thickness of an accumulated grease layer on the interior of the duct.

18 Claims, 5 Drawing Sheets

U.S. PATENT DOCUMENTS

| | | | |
|---|---|---|---|
| 3,890,827 A | 6/1975 | Van Schoyck | |
| 4,180,185 A * | 12/1979 | Yamamoto et al. | 222/57 |
| 4,429,225 A | 1/1984 | Fumoto et al. | |
| 4,524,835 A | 6/1985 | Mingrone | |
| 4,912,332 A | 3/1990 | Siebel et al. | |
| 5,096,502 A | 3/1992 | Carter et al. | |
| 5,112,642 A | 5/1992 | Wajid | |
| 5,536,359 A | 7/1996 | Kawada et al. | |
| 5,618,992 A | 4/1997 | Bond et al. | |
| 5,658,359 A * | 8/1997 | Berg et al. | 48/197 R |
| 5,661,233 A | 8/1997 | Spates et al. | |
| 5,666,394 A | 9/1997 | Swanson | |
| 5,843,232 A | 12/1998 | Savkar et al. | |
| 5,897,378 A | 4/1999 | Eriguchi | |
| 5,985,032 A | 11/1999 | Eriguchi | |
| 6,107,603 A | 8/2000 | Dementhon et al. | |
| 6,124,927 A | 9/2000 | Zhong et al. | |
| 6,170,480 B1 * | 1/2001 | Melink et al. | 126/299 R |
| 6,536,649 B1 * | 3/2003 | Master et al. | 228/49.5 |
| 6,701,787 B2 | 3/2004 | Han et al. | |
| 6,880,402 B1 | 4/2005 | Couet et al. | |
| 7,354,429 B2 * | 4/2008 | Sparks et al. | 604/503 |
| 7,607,825 B2 * | 10/2009 | Koschack et al. | 374/7 |
| 2005/0210960 A1 * | 9/2005 | Shamout et al. | 73/40.5 A |
| 2005/0279084 A1 * | 12/2005 | Schmidt et al. | 60/295 |
| 2006/0037399 A1 * | 2/2006 | Brown | 73/580 |
| 2006/0100796 A1 * | 5/2006 | Fraden et al. | 702/45 |
| 2007/0189356 A1 * | 8/2007 | Pettit et al. | 374/7 |
| 2007/0245703 A1 * | 10/2007 | Randinelli et al. | 55/528 |
| 2008/0100826 A1 * | 5/2008 | Sharpe | 356/51 |

FOREIGN PATENT DOCUMENTS

| | | |
|---|---|---|
| EP | 1 318 211 A1 | 6/2003 |
| GB | 724779 | 2/1955 |
| GB | 815366 | 12/1956 |
| GB | 815347 | 6/1959 |
| GB | 2 455 834 A | 6/2009 |
| JP | S60-033143 U | 3/1985 |
| WO | WO 2007/093374 | 8/2007 |

OTHER PUBLICATIONS

Office Action issued Mar. 4, 2013, in Canadian Patent Application No. 2,690,615.

Office Communication issued Jan. 22, 2013, in European Patent Application No. 08771092.7.

Office Action dated May 15, 2012 in Australian Patent Application No. 2008265939.

* cited by examiner

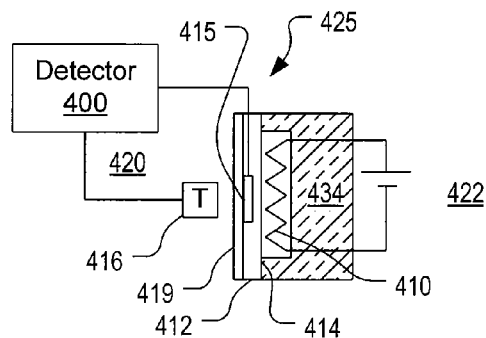
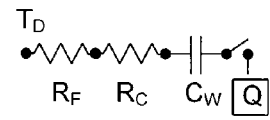
Fig. 4A
Fig. 4B
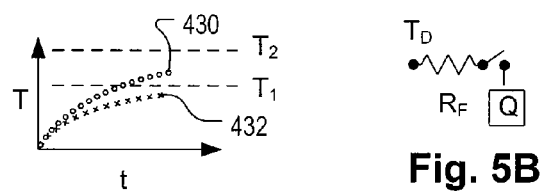
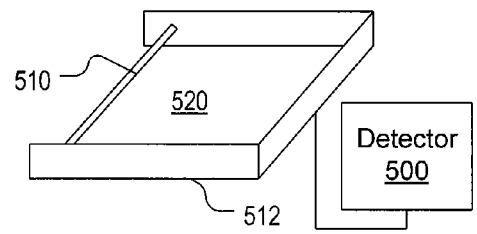
Fig. 4C
Fig. 5B
Fig. 5A
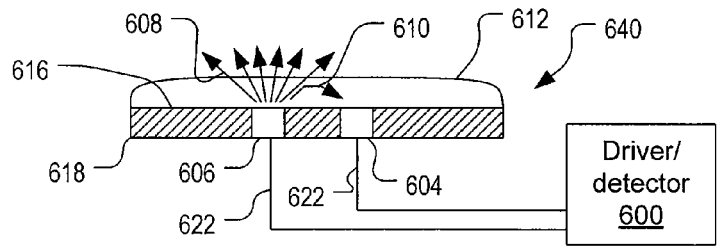
Fig. 6
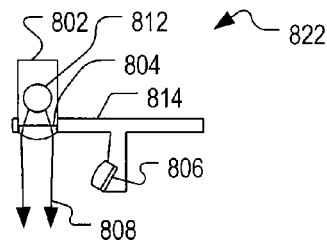
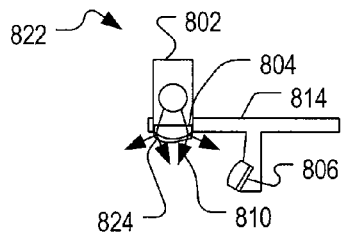
Fig. 7A
Fig. 7B

DUCT GREASE DEPOSIT DETECTION DEVICES, SYSTEMS, AND METHODS

CROSS REFERENCE TO RELATED APPLICATIONS

The present application is a 371 National Stage of International Application No. PCT/US2008/067000, filed Jun. 13, 2008, which claims the benefit of U.S. Provisional Patent Application No. 60/943,626, entitled "Duct Grease Deposit Detection Devices, Systems, and Methods," filed Jun. 13, 2007, and both of the foregoing applications are hereby incorporated by reference in their entireties.

FIELD OF THE INVENTION

The present invention relates to exhaust ventilation systems and, in particular, to exhaust ventilation systems in which material can accumulate inside the exhaust systems causing potential problems, such as fire hazards.

BACKGROUND

Exhaust systems are often used to remove pollutants from a conditioned space. Many of these systems handle aerosols that are imperfectly removed from exhausted air streams permitting the deposit, and accumulation, of materials in exhaust ducting and hoods. For example, kitchen range hoods remove cooking fumes from kitchens. Such fumes often contain grease aerosols that are imperfectly filtered using grease filters. After a long period of operation, some grease inevitably coats the inside of exhaust ductwork. This can pose a fire hazard and have other undesirable consequences.

There are many devices that have been designed and manufactured for removal of fumes from a kitchen. Canopy and backshelf hoods are common types. These are typically situated above a cooking appliance or appliances and connected through an exhaust duct to a roof-mounted fan that draws air through the hood and discharges to the outside ambient air. Removable cartridge grease filters are usually mounted in the hood just preceding the ductwork. These are normally removed periodically from the hood and washed to remove accumulated grease. Such filters are imperfect in that they are effective for removing the largest particulates, but they tend to leave a substantial amount of grease in the exhausted stream. Grease passing the filters accumulates in the ductwork from the hood and can accumulate on the fan and discharge of the exhaust system as well.

Once grease builds up in a duct, it is possible to clean the duct. Various systems for doing this are known. Visual inspection is one means of determining whether a duct is in need of cleaning. Another method of detecting buildup is described in U.S. Pat. No. 3,890,827 for "Method and apparatus for monitoring grease buildup within an exhaust system" which describes removable patches that can be installed in a duct and removed for close inspection to determine how much grease has accumulated on the surface. Multiple patches are mounted as a set and one patch is removed at a time to determine the grease accumulation.

Fire detection and elimination is a well-known solution for exhaust hoods and ducts. Conventional fire detection and suppression systems may be in installed in kitchen exhaust hoods and ductwork. Fire can be suppressed using water or chemical extinguishers. For example, U.S. Pat. No. 4,524,835 for "Fire suppression system" describes a chemical fire suppression system There is a need in the art for convenient and reliable mechanisms for detecting the buildup of grease and other contaminants in ductwork. The known methods relying on visual inspection are tedious and unreliable and also difficult to enforce.

SUMMARY

Automatic devices that determine when pollutant deposits have accumulated in ductwork are employed to notify maintenance personnel or automated cleaning equipment of the need for ducts to cleaned or replaced. Various embodiments of detection devices may be employed which detects a property of accumulated grease and generates an indication of an accumulation from it. In most such devices, preferably, a calibration is performed for the type of material that tends to deposit. In preferred embodiments, the detection device presents a surface to the fume stream inside a duct. In the preferred embodiment, the surface is cooled to a temperature that represents a worst case temperature so that the accumulation (due to condensation) on the detector surface is at least as high as the coolest surface in the ductwork which is being monitored. Also, preferably, the detection device is positioned such that, as nearly as possible, it is in a worst-case position for exposure to grease in the fume stream. So, for example, it may be located in a high velocity position or in a region of a reversing or stagnating boundary layer, depending on the properties of the aerosol stream and the configuration of the ductwork.

In a preferred type of detector, a micro-scale device is used to detect accumulation of grease. Micro-scales are used to measure minute quantities of material by detecting the change in a resonant frequency of an object on which material has been deposited. An example of a micro-scale is one that employs a piezoelectric transducer which is driven over a range of frequencies. By suitably calibrating the device, the change in mass, relative to a baseline, can be determined and compared with a threshold where cleaning is required.

According to an embodiment, the invention is a method for detecting fouling in a duct, comprising: placing a member with a surface in an exhaust stream, and generating a signal indicating a fouled condition of the surface due to a change in a property of the surface indicative of fouling. In another embodiment, the property is at least one of optical opacity, reflectivity, optical scattering, thermal conductivity, and mass. In another embodiment, the placing includes (i.e., comprises) installing a disposable detector, the method further comprising replacing the detector after the generating. In another embodiment, the method includes cooling the surface. In another embodiment, the method includes cooling the surface to a predetermined temperature. In another embodiment, the property includes mass and the generating includes measuring a resonant frequency of the member. In another embodiment, the placing includes orienting the surface so that it faces an oncoming flow of fumes. In another embodiment, the generating includes comparing a measured property trend with a predetermined trend to identify a correlation.

According to another embodiment, the invention is a device which may be used to implement any of the foregoing methods. In an embodiment, the device includes a piezoelectric microscale to measure the mass of material accumulated on the surface.

According to another embodiment, the invention is a system to implement any of the foregoing methods. The system may include a controller to take a sample measurement when an exhaust system is not operating.

According to another embodiment, the invention is a method for detecting a level of accumulated contamination in a duct including (i.e., comprising) providing a detector in fluid communication with an exhaust stream flowing through the duct. The method may further include determining the level of accumulated contamination in the duct using the detector. The method may further include outputting a signal based on the determining. In another embodiment, the method may further include activating an alarm based on the outputting. In another embodiment, the method may further include displaying to a user the level of accumulated contamination based on the outputting. In another embodiment, the detector may include a sensing element having a surface, and a controller which interrogates the sensing element. In another embodiment, the providing may include orienting the surface of the sensing element in the exhaust stream such that the surface is in a worst-case position for exposure to contaminants in the exhaust stream. In another embodiment, the determining may include using the controller, interrogating the sensing element to obtain a measurement indicative of the level of accumulated contamination in the duct. In another embodiment, the method may further include cooling the detector to a target temperature. In another embodiment, the method may further include determining the target temperature according to a real-time model of a wall of the duct, a temperature of the exhaust stream, and/or ambient temperature.

According to another embodiment, a method for detecting fouling in a duct may include placing a detector arrangement external to a duct so as to be physically isolated from an exhaust stream flowing through the duct, interrogating the duct using the detector arrangement to generate a detection result, and correlating the detection result with an amount of accumulated fouling on an interior surface of the duct.

In another embodiment, the detector arrangement may include an acoustic source and an acoustic sensor, said placing may include positioning the acoustic source and the acoustic sensor at a first side on an exterior of the duct, said interrogating may include transmitting an acoustic signal from the source to the first side of the duct and measuring reflected acoustic signals with the acoustic sensor, and said correlating may include calculating an acoustic impedance and relating the acoustic impedance to a thickness of the accumulated fouling.

In another embodiment, the detector arrangement may include a radioactive source and a radioactive sensor, said placing may include positioning the radioactive source and the radioactive sensor at a first side on an exterior of the duct, said interrogating may include transmitting radioactive energy from the radioactive source and measuring radiation with the radioactive sensor, and said correlating may include relating the measured radiation to a thickness of the accumulated fouling.

In another embodiment, the detector arrangement may include a radioactive source and a radioactive sensor, said placing may include positioning the radioactive source at a first side on an exterior of the duct and positioning the radioactive sensor at a second side on the exterior of the duct opposite the radioactive source, said interrogating may include transmitting radioactive energy from the radioactive source and measuring radiation with the radioactive sensor, and said correlating may include relating the measured radiation to a thickness of the accumulated fouling.

Objects, advantages and features of the present invention will become apparent from the following detailed description of the invention when considered in conjunction with the accompanying drawings

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention. Throughout the figures, like reference numerals denote like elements.

FIG. 4A shows a detector which uses a change in thermal properties of a detector surface to identify an accumulation of deposits on the surface.

FIG. 4B shows a network model that may be used to model the response of the detector of FIG. 4A.

FIG. 4C shows a plot of temperature samples for illustrating the operation of the detector of FIG. 4A.

FIG. 5A shows another type of detector which uses a change in thermal properties of a detector surface to identify an accumulation of deposits on the surface.

FIG. 5B shows a network model that may be used to model the response of the detector of FIG. 5A.

FIG. 6 shows an optical detector which relies on scattering within a deposit film to detect the accumulation of a specified amount of material.

FIGS. 7A and 7B show a detector that detects scattering of light caused by accumulation of grease deposits on a detector.

FIG. 10$b$ shows a cantilevered beam with a strain gauge that can indicate accumulation of grease on a detection surface by deflection of the free end.

FIG. 11$b$ shows a schematic of a generalized detector arrangement having a source and sensing element collocated external to the duct for determining an accumulation of fouling material in the duct.

FIG. 11$c$ shows a schematic of a generalized detector arrangement having a source on an opposite side of the duct from the sensing element for determining an accumulation of fouling material in the duct.

DETAILED DESCRIPTION OF EMBODIMENTS

Figure 1:
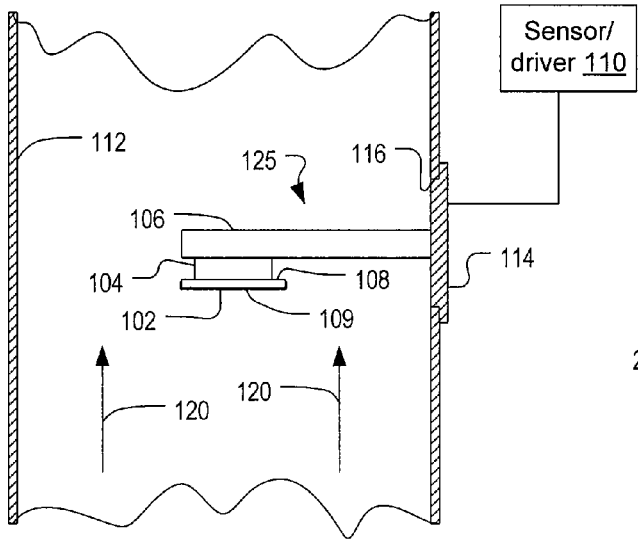
FIG. 1 shows a microscale mounted in a duct with a sensor/driver to detect the accumulation of grease on a detector surface by oscillating the detector surface and determining a change in resonant frequency thereof.

Referring now to FIG. 1, a duct 112 has an opening 116 through which is inserted a fouling detector 125. The fouling detector has a plate 108 with a detection surface 109 protected by a removable protector sheet 102. An oscillator actuator 104, such as a piezoelectric crystal, causes the plate 108 to vibrate relative to a mounting support 106 attached to the duct 112. A gas stream 120, which contains suspended contaminant particles such as grease droplets, passes around the detection surface 109 causing the suspended particles to impinge on the surface. Over time, a coating grows on the detection surface 109. The coating increases the mass of the plate 108 such that the change in mass can be detected by a change in the resonance frequency of the plate. A sensor/drive 110 provides the driving signal to oscillate the plate 108 and to detect the resonant frequency.

Suitable detection devices are known in the art and are frequently used for deposition detection where high sensitivity to low deposition rates are required. One name for such devices is microscales. Examples of the applicable technologies are shown in the following patents each of which is incorporated by reference in its entirety herein: U.S. Pat. No. 6,880,402 for "Deposition monitoring system," U.S. Pat. No. 6,124,927 for "Method to protect chamber wall from etching by endpoint plasma clean," U.S. Pat. No. 5,985,032 for "Semiconductor manufacturing apparatus," U.S. Pat. No. 5,897,378 for "Method of monitoring deposit in chamber, method of plasma processing, method of dry-cleaning chamber, and semiconductor manufacturing apparatus," U.S. Pat. No. 5,843,232 for "Measuring deposit thickness in composite materials production," U.S. Pat. No. 5,661,233 for "Acoustic-wave sensor apparatus for analyzing a petroleum-based composition and sensing solidification of constituents therein," U.S. Pat. No. 5,536,359 for "Semiconductor device manufacturing apparatus and method with optical monitoring of state of processing chamber," U.S. Pat. No. 5,112,642 for "Measuring and controlling deposition on a piezoelectric monitor crystal," U.S. Pat. No. 5,666,394 for "Thickness measurement gauge," U.S. Pat. No. 6,701,787 for "Acoustic sensor for pipeline deposition characterization and monitoring of pipeline deposits," U.S. Pat. No. 5,618,992 for "Device and method for monitoring deposits in a pipe or vessel," U.S. Pat. No. 3,023,312 for "Radioactive pipe thickness measurement," and U.S. Pat. No. 4,429,225 for "Infrared thickness measuring device."

The mass measurements required for detecting deposition films for the present purposes need not be as precise as required in some industries, such as those discussed in the above patents. In addition, substantial masses of material can provide suitable indications of deposit formation such that oscillating systems other than piezoelectric can be made using, for example, speaker coils and spring or other devices.

The protector sheet 102 may be, for example, a plastic sheet with an adhesive backing. By providing the protector sheet 102, the fouling detector can be protected from being permanently coated with material accumulated from the gas stream. The fouling detector 125 may be removed from the duct and the protection sheet 102 replaced at a time after an indication has been generated by the sensor/driver 110. Preferably, the sensor/driver 110 is configured to run a test on a schedule, such as once per day or once every few days. Thus, the sensor/driver 110 can be provided with an alarm or it may be connected to a computer network to signal one or more remote terminals.

Figure 2:
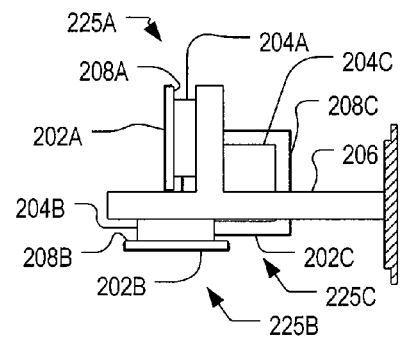
FIG. 2 shows an array of detectors mounted at various angles and positions to mimic multiple duct surfaces on which pollutants may accumulate.

FIG. 2 shows a support 206 holding multiple fouling detectors 225A, 225B, and 225C. Each fouling detector has a surface 202A, 202B, and 202C, a detector portion 204A, 204B, and 204C, which may be an oscillation actuator as in the embodiment of FIG. 1 which measures the mass accumulated on plates 208A, 208B, and 208C. FIG. 2 illustrates that various mounting configurations for fouling detectors, as exemplified by fouling detectors 225A, 225B, and 225C, are possible. Also, FIG. 2 illustrates that multiple fouling detectors may be combined when it is difficult to predict the configuration corresponding to the worst-case propensity for fouling. For example, fouling detector 225A is partially "shaded" from the gas flow by fouling detector 225B. This may induce eddies and stagnation regions which may cause worst-case deposition rates of fumes. The properties of turbulent flow are difficult to predict so that it may not be possible to determine in a real configuration which orientation would produce the worst-case result. Therefore, multiple detectors, each with a different orientation or configuration (for example "shaded") may be employed in a single device. Note that if fouling detector 225A were used alone, a shading member could be used instead.

Other configuration parameters that may be varied include the distance the detector is located downstream of a shading member, the size of the shading member relative to the detector, and the orientation of the shading member (e.g., oblique). Other orientations are also possible such as angled non-rectilinearly and/or non-orthogonally.

Figure 3A:
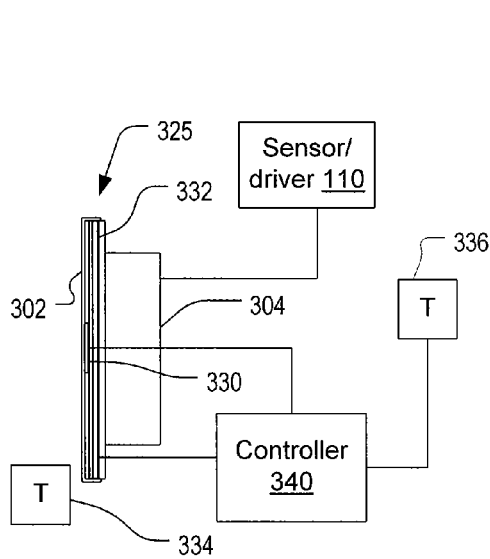
FIG. 3A shows a detector with an active cooling device.

Referring to FIG. 3A, preferably a detector of any given configuration has a deposition surface that models the worst-case characteristics of the duct other than just the orientation of the surface relative to the flow and the type of flow impinging thereon. For example, grease aerosols often deposit when the temperature of the particles reaches a condensation point. Ducting surfaces which are subject to fouling may be cooler than the flue stream and therefore may cause precipitation of material that is in a vapor phase while in the flue stream. To ensure that a detector collects material at least as effectively as the worst-case duct portion, a mechanism for cooling the deposition surface of the detector may be employed. FIG. 3A shows a fouling detector 325 with an active cooling mechanism 332, for example, a thermoelectric cooler. A sensor driver 110 and detector portion 304 serve to measure the mass of accumulated material on a detection surface 302. A thermocouple or thermistor or other suitable temperature sensor 330 may be provided as well as a temperature sensor T 336 for a space surrounding the ductwork.

A controller 340 may, according to known feedback control, regulate a temperature of the detection surface 302 so that its temperature corresponds closely to the worst-case ductwork surface portion, or slightly worse. For example, the temperature may be maintained at the temperature of the lowest air temperature to which the ductwork is exposed. Such temperature, mostly because of film resistance on either side of the duct surface and due to the resistance of insulation, if present, will be lower than any interior duct surface, at least during steady operation. Thus, it may be more representative to use an intermediate temperature between the duct interior (indicated by a temperature sensor 334 for the exhaust flow) and the ambient.

Preferably, the target temperature may be varied in time according to a model of the duct wall, the temperature of the exhaust flow, and/or the ambient temperature such that a real-time worst-case surface temperature is achieved. Such a real-time model may be implemented readily using a programmable processor and based on the indicated temperature inputs as well as the properties of a suitable duct wall model. For example, a one-dimensional thermal model of the duct wall may be derived using known equations for conductive, convective, and radiative heat transfer. For a given exhaust flow rate, measured exhaust flow temperature and ambient temperature may thus be used with the thermal model to derive the temperature of the surface of the duct. Changes in the measured temperatures can then be correlated to changes in the duct surface temperature. This calculated duct surface temperature may then be used as a target temperature for the cooling of the detection surface. The active cooling mechanism may be applied to any of the foregoing or yet-to-be-discussed fouling detector embodiments, or others.

Figure 3B:
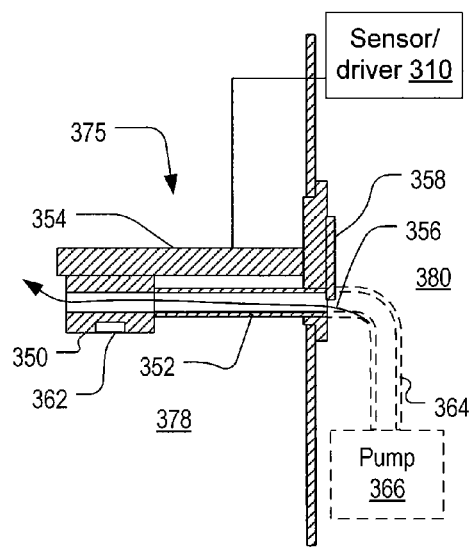
FIG. 3B shows a detector with a passive cooling device.

FIG. 3B shows a passively cooled fouling detector device 375. A support 354 supports a fouling detector 350 in a duct interior 378. A channel 352 conveys ambient air 380 through it into the duct interior 352, which may be at a negative pressure relative to the ambient. The flow of ambient air 380 through the channel 352, which is in contact with the fouling detector 350, cools the fouling detector 350 relative to the duct interior 378 temperature. An adjustable damper blade 358 blocks the flow 356 through the channel 352 to permit it to be regulated. A sensor/driver 310 controls the fouling detector and also may detect a temperature indicated by a temperature sensor 362 to permit an operator to adjust the damper blade 358 based on the fouling detector 350 temperature. An air pump 366 may be used, with a channel extension 364, to force air into the channel 352 if the duct interior 378 is under low negative or positive pressure. The passive cooling mechanism may be applied to any of the foregoing or yet-to-be-discussed fouling detector embodiments, or others.

FIG. 4 shows a fouling detector that employs a thermal effect to determine the quantity of material deposited on a detection surface 412 of a plate 414. A detector 400 monitors one or more temperatures by receiving corresponding signals from temperature sensors, for example sensors 416, 415 which indicate the temperature of the air/gas on a duct side of the plate 414 and the temperature on a heated side of the plate 414. A heater 410 (under control of the detector 400) heats the plate 412 as the temperature of the plate is monitored. Insulation 434 may be provided to reduce cooling of the plate 414 by ambient air 422. As the temperature of the plate 414 rises, it tracks a time vs. temperature profile which corresponds to the insulation generated by a layer of deposit 419 on the detection surface 412. The detector 400 may be configured to perform a test when the exhaust system is powered off, for example, to run the test according to a clock indication that off-operating hours are current or by detecting the status of the exhaust system. Preferably, the test is done when the temperature of the duct-side ambient gas (air) 420 is constant and there is no flow, so that the insulation provided by the layer of deposit 419 can be determined.

FIG. 4B shows a simple one-dimensional network model for an infinite planar heat source whose power output is Q, which transfers heat to a node whose thermal capacitance is CW, and to an infinite sink at the duct air 420 temperature TD through a thermal resistance equal to that of the deposit RC and the film resistance RF on the duct air side 420. Referring also to FIG. 4C, the RC, the quantity that is unknown, can be obtained by solving for the value of RC by fitting a plot (e.g. 430 corresponding to a high value of RC or 432 corresponding to a low value of RC) of the measured temperatures to the unsteady model (t indicating time). Equivalently, a steady state temperature (e.g., T1, T2) derived from an interpolation and used in the steady state model. Note that the model may take into account of the change in film coefficient with temperature due to thermal convection, so RF may be a function of temperature and time. For RF, the thickness of the deposited layer may be obtained from calibration data obtained using samples of deposited material.

FIG. 5A shows a thermal fouling detector that corresponds to a simpler model than the one of FIG. 4A. It uses a heated wire 510 whose surface serves as the detection surface. The network model shown in FIG. 5B is one-dimensional as in the previous embodiment (and there is a planar equivalent, which is an alternative embodiment). Here, the heat source may be a conducting film over an electrical and thermal insulator. A material with known variation of electrical resistance with temperature may be used, for example platinum. By measuring the voltage and current using a detector 500, the power dissipation rate and temperature may be obtained and measured over time from a starting time. As in the previous example, by fitting the temperature measurements to a suitable model of the system, the unknown value of RF may be derived and, from that, the thickness of the deposited layer.

FIG. 6 shows an optical fouling detector 640 which has a plate 618 with an illumination source 606 and a light sensor 604. A driver/detector 600 powers the illumination source, for example a light emitting diode with a lens, such that the illumination source directs light in a direction normal to a detection surface 616 when no material is deposited on the surface. When material accumulates on the surface as indicated at 612, light from the illumination source 606 is scattered in the material layer 612 and received by the light sensor 604 as indicated by scattered beam 610. The greater the thickness of the material layer 612, the greater the scattering and the more light is received by the light sensor 604. The driver/detector 600 may be configured to generate an indication of a specified degree of fouling when a threshold quantity of scattered light is detected thereby. The illumination source 606 and light sensor 604 may be complete devices that generate electrical signals through lines 622 or they may be terminals of fiber optic channels also represented by 622. In the latter case, they may be located very close together. In addition, illumination source 606 and light sensor 604 constitute one pair or there may be more than one of either or both.

FIGS. 7A and 7B show another type of optical fouling detector 822 in which a light source 802 directs light such that it does not fall on a detector 806 when the surface of a lens or window 804 is clean, as indicated by arrows (representing beams) 808. When the surface of the lens or window 804 becomes coated with deposited material, the light from the light source 802 scatters as indicated by arrows 810. Some of the scattered light falls on the detector 806. A driver/detector (not shown) functions as in the embodiment of FIG. 6, generating an indication of a predefined degree of fouling after the quantity of light falling on the detector 806 reaches a threshold. A support 814 can hold both the light source 802 and the detector 806 in position within the duct.

Note that the detector 822 may be constructed of low cost materials and design such that it can be replaced each time the duct is cleaned. Thus, the device 822 generates a single indication and then is replaced. The driver/detector associated with it may be a permanent component. A disposable detector may be preferable to avoid the consequences of improper cleaning or change in performance characteristics of the fouling detector over time. All of the discussed embodiments may include single-use disposable components as discussed with regard to FIGS. 7A and 7B.

Note that in both of the embodiments of FIGS. 6 and 7A, 7B, rather than triggering an indication of fouling based solely on total amount of light falling on the detector due to scattering, a light intensity curve can be obtained and memorized over time and compared with a representative profile for a detection surface that has become fouled. This may be preferable where the deposited material is not highly transmissive in its dried form, for example, if grease particles contained soot. In such a case, a representative profile may be one where the light intensity on the detector reaches a peak at a certain point in time and then decays due to further blocking by the deposited material. The fouling detection indication may be generated by detecting the peak or, in addition, after a drop in the light intensity that follows it of a certain amount.

Figure 8A:
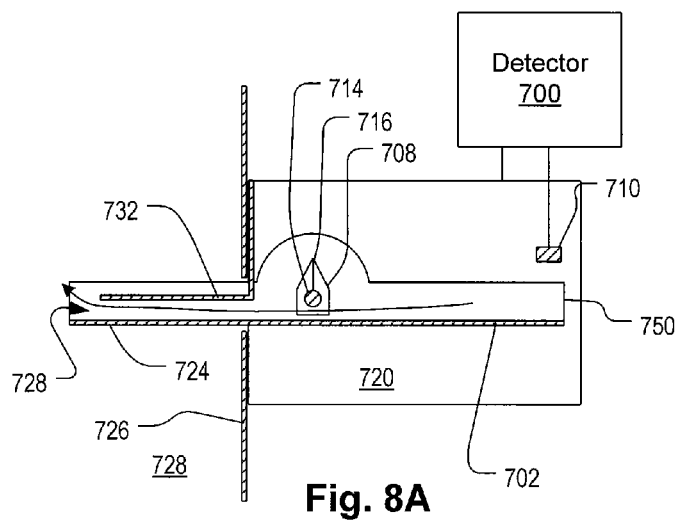
FIGS. 8A and 8B show a passively cooled mechanical balance that can indicate the accumulation of grease on a detection surface by tilting.
Figure 8B:
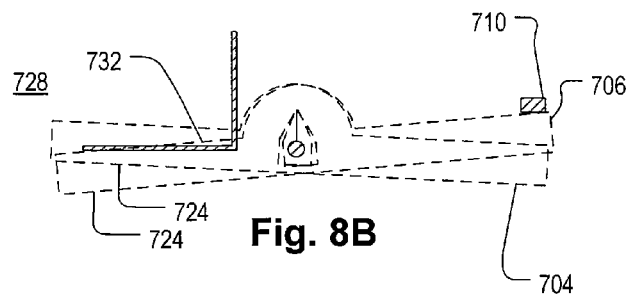

FIGS. 8A and 8B show a balance device in which a balance 750 has a detection surface 724 exposed to fumes 728 in a duct 726 and a portion 702 outside or shielded from the fumes 728 in the duct 726. The balance has a rectangular channel shape (but could be other shapes as well) such that a wall 732 projects into a recess defining a flow path 728 between the wall 732 and the balance 750. Air from outside the duct flows through the flow path 728 to cool the detection surface 724 when fumes flow through the duct 726. The balance 750 pivots on a knife 714 which is located by a notch 716 defined by an opening 708 such that when the detection surface 724 is clean, the detection surface 724 is horizontal due to a balanced state. Since the pivot point coinciding with the notch 716 is above the center of gravity, the balance 750 will come to equilibrium at different angles depending on how much mass accumulates on the detection surface 724. The wall 732 prevents the balance 750 from pivoting too far due to dynamic pressure from the fumes 728 during operation of the exhaust system such that the detection surface 724 always remains substantially level as indicated by the outline 704 in FIG. 8B. When a certain amount of material is deposited on fouling surface 724, the balance 750 is tipped until contact between it and a contact 710 is made, completing a circuit and triggering an indication of a fouled condition. As in previous embodiments, the test may be performed only when the exhaust system is not operating according to a clock or a detector of the exhaust system state. The detector 700 may be configured such that a constant closed circuit for a minimum period of time must be maintained in order to generate an indication of a fouled condition. The wall 732 and/or knife 714 may include one or more electrical insulators depending on how the electrical circuit is defined by the structure. As in previous embodiments, the balance may be a disposable component which is replaced after a fouled state is indicated.

Figures 9A, 9B:
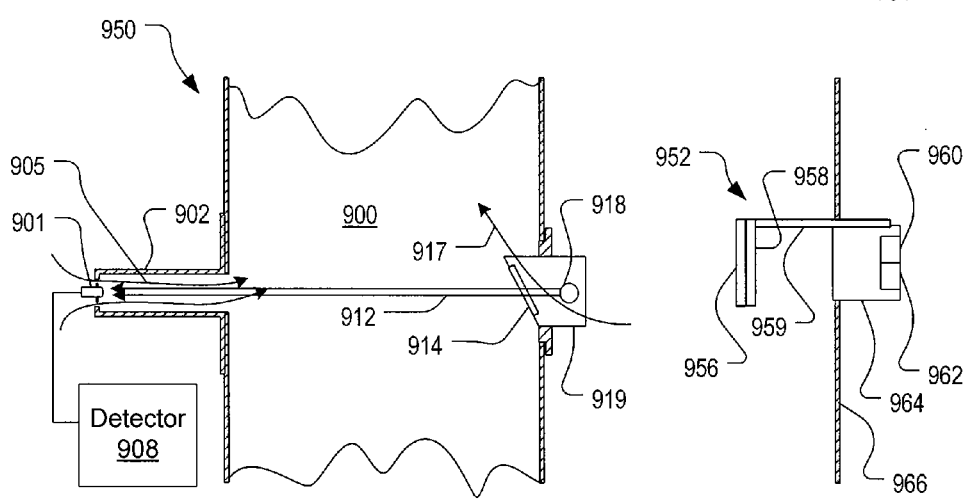
FIGS. 9A and 9B shows other types of optical devices that indicates the accumulation of material by detecting a change in opacity.

FIG. 9A shows another optical type of fouling detector in which opacity caused by a deposited film is detected and a degree of occultation used as a basis for indicating a fouled condition. A light source 918 shines a light through a window 914 toward a detector 901 located in a well 902. Air 905 is drawn through the well 902 to keep material from fouling the detector 901. Light is projected as indicated by arrows 912 toward the detector 901 generating a signal indicative of the amount of light which is received by a detector control 908, which generates a fouled condition indication when the amount of light received falls below a threshold level. The window 914 may be cooled by a flow of air as indicated by arrow 917 by providing appropriate openings in the housing 919. The detector 901 and the light source 918 are located on opposite sides of a duct 900 so that fumes are deposited on the window 914. FIG. 9B shows an alternative embodiment of a fouling detector 952 which does not require that portions of the detector be located on opposite sides of the duct. A light source 960 directs light toward a mirror 958 which is reflected back to a detector 962. The mirror 958 is supported by a low profile arm 958 so that exhaust can flow around it easily causing material in the exhaust to be deposited on the mirror 958. The fouling detector 952 can be placed in a single access opening of a duct wall 966. An active or passive cooling mechanism 956 may be provided. The fouling detector 952 can be configured such that the mirror is located at nearly any desirable angle or positioning the light source 960 and the detector. The angle of the mirror can be non-critical if replaced by a diffuse reflector or retroreflector material (typically a bed of spherical particles that return light to the source irrespective of the orientation of the bed).

Figure 10A:
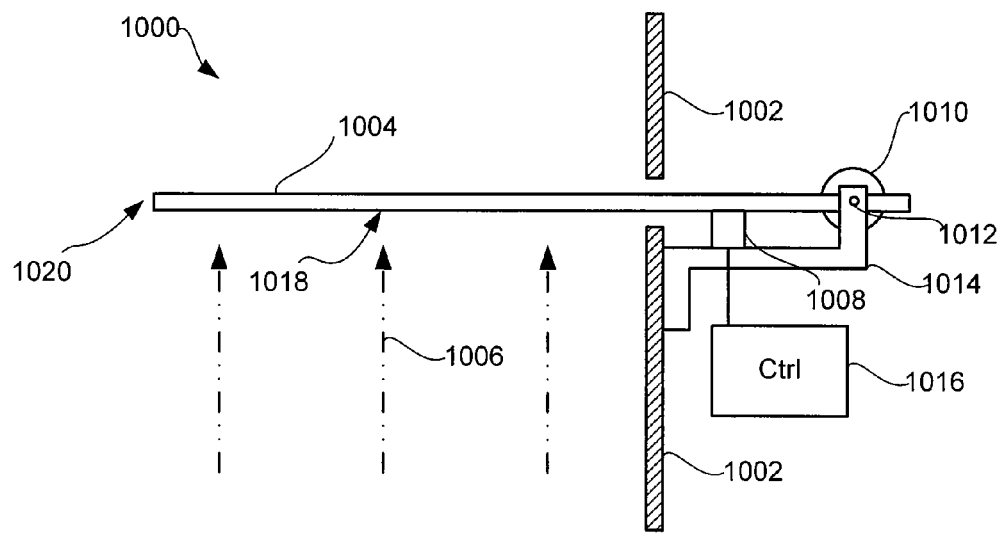
FIG. 10$a$ shows a lever with a strain gauge that can indicate the accumulation of grease on a detection surface by deflection of the free end.

FIG. 10a shows another embodiment for a fouling detector 1000 employing a lever 1004 with a sensor 1008 that can indicate the accumulation of grease on a detection surface 1018 by deflection of the free end 1020. The lever 1004 is rotatably fixed at pivot point 1012. A spring 1010 is provided about pivot point 1012 and adjusted to hold the lever in a parallel orientation when no grease has accumulated on the lever. Support 1014 holds the lever 1004 via pivot point 1012 and spring 1010 at a fixed position with respect to duct wall 1002. As grease in flow 1006 within the duct accumulates on the detection surface 1018, the increased mass of the lever 1004 causes the lever to rotate about pivot 1012 in a counterclockwise manner. A sensor 1008 may be provided in contact with the lever 1004 at a position outside of duct wall 1002. For example, the sensor 1008 may be a strain gauge. In another example, sensor 1008 may be a force sensor. In yet another example, sensor 1008 may be a displacement sensor, such as a capacitive sensor. The sensor 1008 generates a signal indicative of movement of the lever due to the additional mass of the accumulated grease on the detection surface 1018. The controller 1016 may then use the signal to determine a fouling condition of the duct, such as the amount of grease accumulated on the detection surface.

Figure 10B:
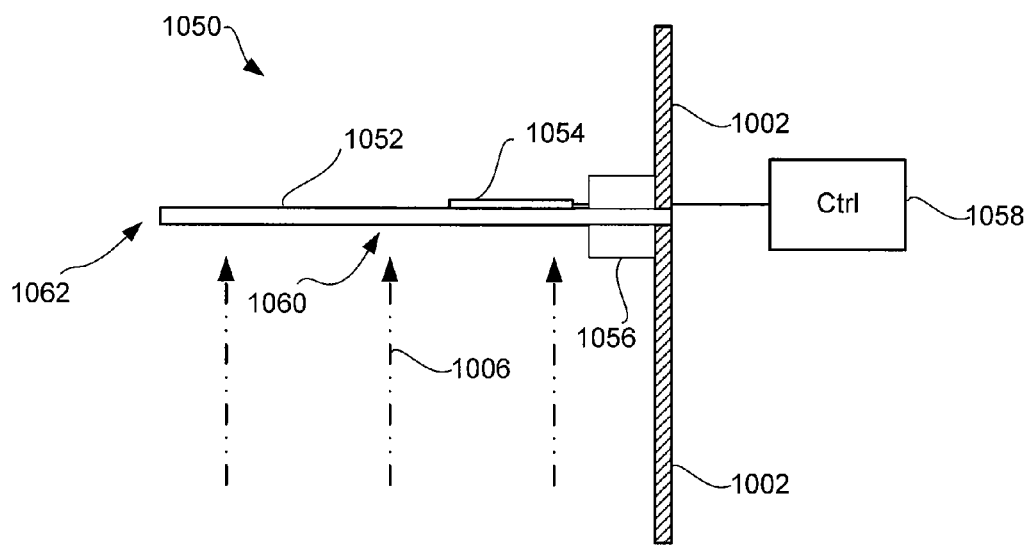

FIG. 10b shows another embodiment for a fouling detector 1050 employing a cantilevered beam 1052 with a strain gauge 1054 that can indicate the accumulation of grease on a detection surface 1060 by deflection of the free end 1062. Support 1056 rigidly fixes the cantilever 1052 adjacent to the duct wall 1002. As grease in flow 1006 within the duct accumulates on the detection surface 1060, the increased mass of the cantilever 1052 causes the cantilever to bend. A strain gauge 1054 is provided on a top (or bottom) surface of the cantilever to determine the amount of bending. Calibration of the strain gauge measurement would be necessary to compensate for the natural bending of the cantilever due to its own weight. The strain gauge 1054 thus generates a signal indicative of the degree of bending of the cantilever due to the additional mass of the accumulated grease on the detection surface 1060. A controller 1058 may then use the signal to determine a fouling condition of the duct, such as the amount of grease accumulated on the detection surface.

Figure 11A:
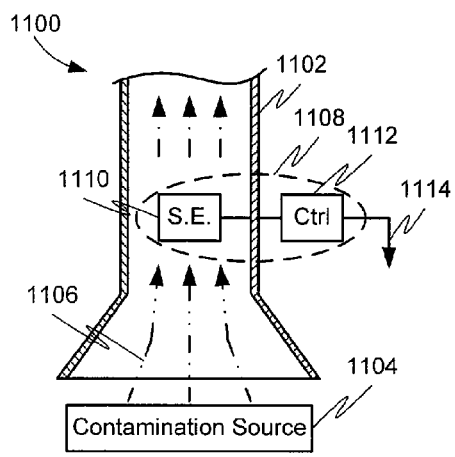
FIG. 11$a$ shows a schematic of a generalized detector arrangement having a sensing element within the duct for determining the accumulation of fouling material in the duct.

FIG. 11a shows a generalized schematic 1100 of a fouling detector arrangement 1108. An air conveyance 1102, such as an exhaust duct, is used to carry an exhaust stream 1106 from a source of contamination 1104, such as a cooking appliance. Exhaust stream 1106 may carry aerosols, such as grease aerosols, which may be deposited on interior surfaces of the air conveyance 1102. A fouling detector arrangement 1108 may be provided to detect the deposition of aerosols or other pollutants. In particular, fouling detector arrangement 1108 may include a sensing element 1110 and a controller 1112.

Sensing element 1110 may be disposed within the exhaust stream 1106 in air conveyance 1102 to allow aerosols or pollutants to interact therewith. For example, sensing element 1110 may have a detection surface exposed to the exhaust stream 1106 which accumulates aerosols and/or pollutants resulting in a change in a property of the detection surface.

Controller 1112 may be functionally connected to the sensing element 1110. The controller 1112 may interrogate the sensing element 1110 to obtain a measurement indicative of the level of accumulated aerosol and/or pollutants within the duct. For example, controller 1112 may interrogate sensing element 1110 to determine a change in mass of the detection surface. Controller 1112 may also be configured to provide a subsequent output 1114 based on the interrogation. For example, controller 1112 may activate an alarm system if the amount of accumulated contamination exceeds a predetermined threshold. Controller 1112 may also display a level of accumulated contamination to a user. Such display may take the form of a number or a color-coded display indicating a relative safety level (e.g., green may indicate safe to operate, yellow may indicate clean air conveyance soon, and red may indicate unsafe to operate). Controller 1112 may also provide an output 1114 to other systems, such as an automatic air conveyance cleaning system to provide for cleaning of the air conveyance 1102 when accumulated contamination levels reach a predetermined threshold.

Figure 11B:
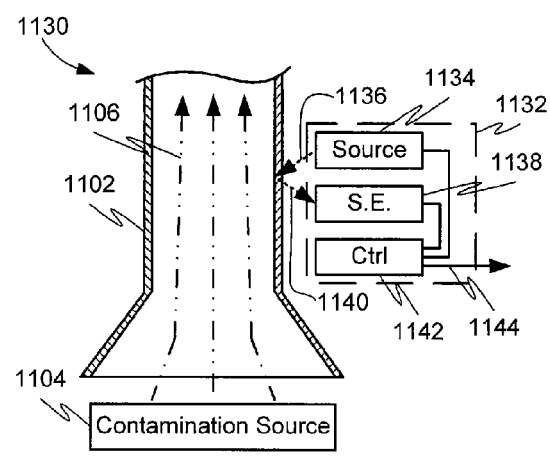

FIG. 11b shows a generalized schematic 1130 of a fouling detector arrangement 1132. An air conveyance 1102, such as an exhaust duct, is used to carry an exhaust stream 1106 from a source of contamination 1104, such as a cooking appliance. In contrast to the schematic of FIG. 11a, the fouling detector arrangement 1132 of FIG. 11b may be provided external to the air conveyance 1102 to detect deposition of aerosol or other pollutants on the air conveyance walls. In particular, fouling detector arrangement 1132 may include a source 1134, a sensing element 1138, and a controller 1142. Thus, the fouling detector arrangement 1132 is isolated from the contaminants in the exhaust stream 1106. The source 1134 interrogates the surface of the air conveyance 1102 by generating a signal 1136 and the sensing element 1138 measures the result 1140 of the interrogation to determine the amount of contaminant accumulated on the surface of the air conveyance 1102. For example, source 1134 may be a source of acoustic or electromagnetic radiation. The radiation is modified in some form and measured by the sensing element 1138. Note that both the source 1134 and sensing element 1138 may be located on the same side of the air conveyance 1102 and preferably oriented such that radiation emanating from the source 1134 and modified by the air conveyance 1102 can be received by sensing element 1138. Controller 1142 may be functionally connected to the sensing element 1138 and may use the measurement of the sensing element to determine a level of accumulated contaminants within the air conveyance 1106. Similar to controller 1112 in FIG. 11a, controller 1142 may also be configured to provide a subsequent output 1144 based on the determination of the level of accumulated contaminants.

In a particular embodiment, the source 1134 may be an acoustic transmitter and the sensing element 1138 may be an acoustic sensor. The acoustic transmitter may generate an acoustic signal. The acoustic signal interacts with the air conveyance and is reflected. A first reflection occurs at the external surface of the air conveyance. A second reflection occurs at the internal surface of the air conveyance. A third reflection occurs at the surface of the contamination layer accumulated on the internal surface of the air conveyance. The reflected signals are received by the acoustic sensor. The controller may then use the received reflected signals to calculate acoustic impedance, as discussed, for example, in U.S. Pat. No. 6,701,787, which is incorporated by reference herein in its entirety. The acoustic impedance may then be correlated to the thickness of the deposited layer.

In yet another embodiment, the source 1134 may be a radioactive source and the sensing element 1138 may be a slow neutron detector. For example, neutrons from a radioactive source may be allowed to interact with a wall of the duct having an accumulated contamination on an interior surface thereof. Fast moving neutrons penetrate the pipe wall without significant interaction and may be elastically scattered by hydrogen or carbon atoms in the contamination. The scattering slows the neutrons, causing some neutrons to be reflected and/or diffuse back towards the radioactive source. A detector, such as a $BF_3$ slow neutron detector, may be placed in proximity to the radioactive source in a position to measure the reflected and/or diffused slow neutrons. The detected slows neutrons thus provide an indication of the thickness of the accumulated contamination.

In yet another example, the source 1134 may be an electromagnetic radiation source, such as an infrared (IR) transmitter, and the sensing element 1138 may be an electromagnetic radiation sensor. The IR transmitter may generate an IR signal. The IR signal interacts with the air conveyance and is reflected and/or absorbed by the materials it encounters. A first reflection occurs at the external surface of the air conveyance. A second reflection occurs at the internal surface of the air conveyance. A third reflection occurs at the surface of the contamination layer accumulated on the internal surface of the air conveyance. The reflected signals are received by the electromagnetic radiation sensor. The controller may then use the received reflected signals to calculate the thickness of the deposited layer.

Figure 11C:
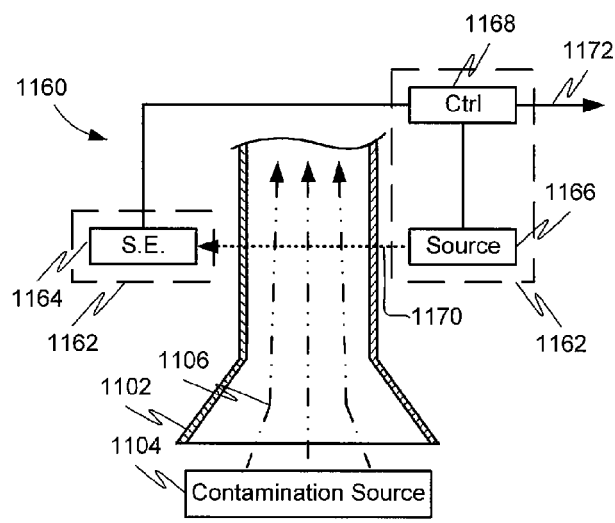

FIG. 11c shows a generalized schematic 1160 of a fouling detector arrangement 1162. An air conveyance 1102, such as an exhaust duct, is used to carry an exhaust stream 1106 from a source of contamination 1104, such as a cooking appliance. Fouling detector arrangement 1162 may include a source 1166, a sensing element 1164, and a controller 1168 external to the air conveyance 1102. Thus, the fouling detector arrangement 1162 is isolated from the contaminants in the exhaust stream 1106. In contrast to the schematic of FIG. 11b, the fouling detector arrangement 1162 of FIG. 11c may be provided with source 1166 located at an opposite side of the air conveyance 1102 with respect to the sensing element 1164.

The source 1166 interrogates the surfaces of the air conveyance 1102 by generating a signal 1170 and the sensing element 1164 measures the signal 1170, as modified by the air conveyance 1102, to determine the amount of contaminant accumulated on the surface of the air conveyance 1102. For example, source 1166 may be a source of acoustic or electromagnetic radiation. The radiation is modified in some form and measured by the sensing element 1164. Note that both the source 1166 and sensing element 1164 are located opposite each other and preferably oriented such that radiation emanating from the source 1166 and modified by the air conveyance 1102 can be received by sensing element 1164. Controller 1168 may be functionally connected to the sensing element 1164 and may use the measurement of the sensing element to determine a level of accumulated contaminants within the air conveyance 1102. Similar to controller 1112 in FIG. 11a, controller 1168 may also be configured to provide a subsequent output 1172 based on the determination of the level of accumulated contaminants.

In a particular embodiment, the source 1166 may be an acoustic transmitter and the sensing element 1164 may be an acoustic sensor. The acoustic transmitter may generate an acoustic signal. The acoustic signal interacts with the air conveyance and is reflected. The transmitted signal through the air conveyance 1102 is received by the acoustic sensor. The controller may then use the received transmitted signal to calculate the thickness of the deposited layer.

In yet another example, the source 1166 may be an electromagnetic radiation source, such as an infrared (IR) transmitter, and the sensing element 1164 may be an electromagnetic radiation sensor. The IR transmitter may generate an IR signal. The IR signal interacts with the air conveyance and is selectively absorbed by the materials encountered in traversing the air conveyance. The attenuated transmitted signal is received by the electromagnetic radiation sensor. The controller may then use the received attenuated signals to calculate the thickness of the deposited layer.

Any of the foregoing embodiments may employ an active or passive cooling mechanism as described with reference to certain embodiments. Any of the above embodiments may take samples during periods of non-operation of the exhaust system based on indications of a clock, an exhaust system state detection (fan power signal, for example), and/or manually. Any of the above embodiments may sample the detected property at intervals and store the values to obtain a trend and use the trend pattern to identify the fouled condition, rather than an instantaneous state. The trend may be derived by studying the properties of the indicator signal compared to the fouling status of the detection surface and providing an appropriate reference to the control. Fouling by different kinds of uses of the exhaust system, which may not be known in advance, may produce different types of results, each associated with a corresponding response by the fouling detector so preferably these variations are taken into account to improve upon the accuracy of the fouled condition indication.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What we claim is:

1. A method for detecting fouling in a duct, comprising:
    placing a member in an exhaust duct of an kitchen exhaust hood with a surface in an exhaust stream flowing in said duct;
    the kitchen exhaust hood receiving fumes containing filterable particles of flammable grease;
    the kitchen exhaust hood having a particulate filter at a position upstream of said member and effective to filter out said filterable particles; and
    generating an output signal indicating a fouled condition of the surface due to a change in a property of the surface indicative of fouling;
    wherein the output signal is generated by a detector that includes a light source and a light detector, the member having a planar surface facing the light source and the light detector, the member being oriented and positioned to reflect light from said light source to said light detector, the member being positioned inside the duct;
    wherein said light source and said light detector being positioned adjacent each other and opposite said member planar surface;
    wherein said duct having a generally planar wall, said light source and said light detector being on an opposite side of said planar wall from an interior of said duct and said member surface being positioned on n interior side of said planar wall such light detector and the light source are located together opposite the member surface so the member can be placed in a single access opening of the planar wall with he light source and light detector outside the planar wall.

2. The method of claim 1, wherein the property is reflectivity.

3. The method of claim 1, wherein the placing includes installing a disposable detector, the method further comprising replacing the detector after the generating.

4. The method of claim 1, further comprising cooling the surface.

5. The method of claim 1, wherein said generating includes directing light from a light source at said member and detecting light reflecting from said member, using a light detector, generating a received signal from said light detector responsive to the reflectivity of the member and generating said output signal responsively to said received signal.

6. The method of claim 1, wherein placing includes orienting the surface so that it faces an oncoming flow of fumes.

7. The method of claim 1, wherein the generating includes comparing a measured property trend with a predetermined trend to identify a correlation.

8. A device which may be used to implement the method of claim 1.

9. A system which may be used to implement the method of claim 1.

10. A system as in claim 9, wherein a controller is used to take a sample measurement when an exhaust system is not operating.

11. A method for detecting a level of accumulated contamination in a duct, comprising:
    receiving cooking fumes from a cooking process in a kitchen exhaust hood and conveying the cooking fumes to the duct;
    filtering grease particles from the fumes and subsequently conveying filtered product into the duct;
    providing a detector in fluid communication with an exhaust stream flowing through the duct at a location downstream of a point of filtering said grease particles;
    using the detector, determining the level of accumulated contamination in the duct;
    the detector including a light source, a light detector and a member with a planar surface facing the light source, the light source, light detector, and member being oriented and positioned to reflect light from said light source to said light detector, the member being positioned inside the duct;
    said light source and said light detector being positioned adjacent each other and opposite said member planar surface;
    said duct having a generally planar wall, said light source and said light detector being on an opposite side of said planar wall from an interior of said duct and said member surface being positioned on an interior side of said planar wall such light detector and the light source are located together opposite the member surface so the member can be placed in a single access opening of the planar wall with the light source and light detector outside the planar wall;
    said and
    outputting a signal based on the determining.

12. The method of claim 11, further comprising activating an alarm based on said outputting.

13. The method of claim 11, further comprising displaying to a user the level of accumulated contamination based on said outputting.

14. The method of claim 11, wherein said providing includes orienting the surface of the sensing element in the exhaust stream such that the surface is in a worst-case position for exposure to contaminants in the exhaust stream.

15. The method of claim 11, wherein said determining includes, using the controller, interrogating the sensing element to obtain a measurement indicative of the level of accumulated contamination in the duct.

16. The method of claim 11, further comprising cooling the detector to a target temperature.

17. The method of claim 16, further comprising determining the target temperature according to a real-time model of a wall of the duct, a temperature of the exhaust stream, and ambient temperature.

18. The method of claim 1 wherein said member is planar and has a surface material that is identical to that of said duct.

\* \* \* \* \*